United States Patent [19]

Lesher et al.

[11] 4,264,603

[45] Apr. 28, 1981

[54] 5-(PYRIDINYL)-1H-PYRAZOLO[3,4-b]PYRIDINE-3-AMINES, THEIR USE AS CARDIOTONICS AND THEIR PREPARATION

[75] Inventors: George Y. Lesher; Monte D. Gruett, both of Schodack, N.Y.

[73] Assignee: Sterling Drug Inc., New York, N.Y.

[21] Appl. No.: 131,227

[22] Filed: Mar. 17, 1980

[51] Int. Cl.³ ................ C07D 471/02; A61K 31/415
[52] U.S. Cl. .................................. 424/256; 546/119; 546/257; 546/258
[58] Field of Search .................. 546/119; 424/256

[56] References Cited

U.S. PATENT DOCUMENTS

| | | |
|---|---|---|
| 3,423,414 | 1/1969 | Blatter .................... 546/119 |
| 3,872,133 | 3/1975 | Fleckenstein et al. ............ 546/119 |
| 4,004,012 | 1/1977 | Lesher et al. ................ 546/257 X |
| 4,072,746 | 2/1978 | Lesher et al. ................ 546/257 X |
| 4,107,315 | 8/1978 | Lesher et al. ................ 546/257 X |

FOREIGN PATENT DOCUMENTS 2232038 1/1974 Fed. Rep. of Germany ............ 546/119

OTHER PUBLICATIONS

C.A.; 87, (1977), 39357t, Balicki et al.
Balicki et al.; Acta Poloniae Pharmaceutica, (1976), vol. 33 (3), pp. 289-293.
Nantka-Namirski et al.; Pol. J. Pharmacol. Pharm., (1978), vol. 30, pp. 707-712.

*Primary Examiner*—Joseph Paul Brust
*Attorney, Agent, or Firm*—Robert K. Bair; B. Woodrow Wyatt

[57] ABSTRACT

1-R-5-PY-6-Q-1H-pyrazolo[3,4-b]pyridin-3-amines or pharmaceutically-acceptable acid-addition salts thereof, which are useful as cardiotonics, are prepared by reacting a 2-halo-5-PY-6-Q-nicotinonitrile with 1-R-hydrazine, where R is hydrogen, lower-alkyl, lower-hydroxyalkyl, 2,3-dihydroxypropyl or lower-alkoxyalkyl, Q is hydrogen or lower-alkyl, and PY is 4- or 3-pyridinyl or 4- or 3-pyridinyl having one or two lower-alkyl substituents. Also shown are cardiotonic compositions and method for increasing cardiac contractility using said compounds or salts.

11 Claims, No Drawings

5-(PYRIDINYL)-1H-PYRAZOLO[3,4-b]PYRIDINE-3-AMINES, THEIR USE AS CARDIOTONICS AND THEIR PREPARATION

CROSS-REFERENCE TO RELATED APPLICATIONS

The 1,2-dihydro-2-oxo-5-(pyridinyl)-6-(lower-alkyl)-nicotinonitriles diclosed herein as intermediates are disclosed and claimed as cardiotonics and as intermediates in copending U.S. patent application Ser. No. 97,504, filed Nov. 26, 1979.

BACKGROUND OF THE INVENTION (a) Field of the Invention

This invention relates to pyrazolo[3,4-b]pyridin-3-amines, their preparation and their use as cardiotonics.

(b) Description of the Prior Art

Chemical Abstracts Vol. 87, item 39,357t, 1977, reads as follows:

"Dipyridyls. VII. Reaction of β-ketoaldehydes with cyanoacetic acid hydrazide. Balicki, Roman; Kaczmarek, Lukasz; Nantka-Namirski, Pawel (Inst. Org. Chem., Pol. Acad. Sci., Warsaw, Pol.). Acta Pol. Pharm. 1976, 33(3), 289–93 (Pol). RCOCH$_2$CHO (R=Me, Ph, 3- and 4-pyridyl, and

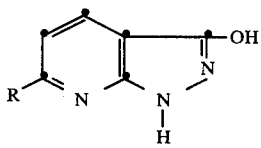

6-methyl-3-pyridyl) condensed in an alk. medium with NCCH$_2$CONHNH$_2$ (I) to give the pyrazolpyridines II. II were also obtained when 5-amino-3-pyrazolone was used instead of I. II (R=3- and 4-pyridyl) were also prepd. in the reaction of Me 6-(3- and 4-pyridyl)-2-chloronicotinates or 6-(3- and 4-pyridyl)-2-chloro-3-cyanopyridines with 80% Nh$_2$Nh$_2$.H$_2$O."

The original article (p. 291) shows that the compounds of formula II (supra) can also exist in tautomeric 1,2-dihydro-6-R-2H-pyrazolo[3,4-b]pyridin-3-one form.

In a later paper entitled "Cancerostatics III. Synthesis and Some Chemical Transformations of 3-Cyano-5-(pyridyl-4)pyrid-2-one" [Pol. J. Pharmacol. Pharm. 30, 707–712 (1978)], P. Nantka-Namorski and L. Kaczmarek show, inter alia, the reaction of 3-cyano-5-(4-pyridinyl)pyridin-2-one [alternatively named 1,2-dihydro-2-oxo-5-(4-pyrridinyl)nicotinitrile] with phosphorus oxychloride to prepare 2-chloro-3-cyano-5-(4-pyridinyl)pyridine [alternatively named 2-chloro-5-(4-pyridinyl)nicotinonitrile].

SUMMARY OF THE INVENTION

In a composition of matter aspect, the invention relates to 1-R-5-PY-6-Q-1H-pyrazolo[3,4-b]pyridin-3-amines or pharmaceutically-acceptable acid-addition salt thereof, where R, PY and Q are defined hereinbelow, which are useful as cardiotonic agents.

The invention in a process aspect comprises reacting 2-halo-5-(pyridinyl)-6-Q-nicotinonitrile with a 1-R-hydrazine to produce a 1-R-5-PY-6-1H-pyrazolo[3,4-b]pyridin-3-amine.

A composition aspect of the invention relates to a cardiotonic composition for increasing contractility in a patient, said composition comprising a pharmaceutically-acceptable carrier and, as the active ingredient thereof, an effective amount of a cardiotonic 1-R-5-PY-6-Q-1H-pyrazolo[3,4-b]pyridin-3-amine or pharmaceutically-acceptable acid-addition salt thereof.

In a method aspect, the invention relates to a method for increasing cardiac contractility in a patient requiring such treatment which comprises the administration of a medicament comprising a pharmaceutically-acceptable carrier and, as the active component, thereof, an effective amount of a cardiotonic 1-R-5-PY-6-Q-1H-pyrazolo[3,4-b]pyridin-3-amine or pharmaceutically-acceptable acid-addition salt thereof.

DETAILED DESCRIPTION INCLUSIVE OF PREFERRED EMBODIMENTS

In a composition of matter aspect the invention resides in a 1-R-5-PY-6-Q-1H-pyrazolo[3,4-b]pyridin-3-amine having formula I

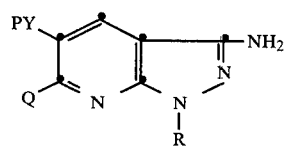

where R is hydrogen, lower-alkyl, lower-hydroxyalkyl, 2,3-dihydroxypropyl or lower-alkoxyalkyl, Q is hydrogen or lower-alkyl, and PY is 4- or 3-pyridinyl or 4- or 3-pyridinyl having one or two lower-alkyl substituents, or pharmaceutically-acceptable acid-addition salt thereof. The compounds of formula I are useful as cardiotonic agents, as determined by standard pharmacological evaluation procedures. Preferred embodiments are those of formula I where PY is 4-pyridinyl or 3-pyridinyl, R is hydrogen, methyl, ethyl or 2-hydroxyethyl, and Q is hydrogen, methyl or ethyl. A particulary preferred embodiment is the compound of formula I where R is 2-hydroxyethyl, Q is hydrogen or methyl and PY is 4-pyridinyl or pharmaceutically-acceptable acid-addition salt thereof.

The compound of formula I may exist in tautomeric forms, that is, as the 1-R-5-PY-6-Q-1H-pyrazolo[3,4-b]pyridin-3-amine of formula I and/or 1-R-1,2-dihydro-5-PY-6-Q-pyrazolo[3,4-b]pyridin-3-imine of formula IA, illustrated as follows:

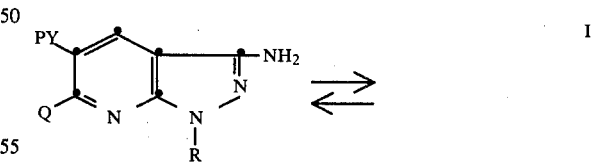

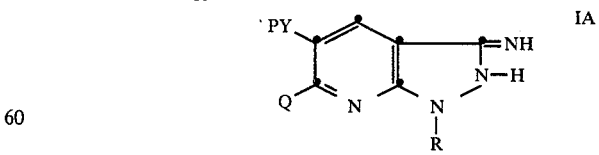

Structural preferences for other known pyrazolo[3,4-b]pyridin-3-amines would indicate the above formula I to be the preferred tautomeric structure; thus, it is preferred to use the names based on structure I, although it is understood that either or both structures are comprehended herein.

In a process aspect the invention resides in the process of producing the 1-R-5-PY-6-Q-1H-pyrazolo[3,4-b]pyridin-3-amine of formula I which comprises reacting 2-halo-5-PY-6-Q-nicotinonitrile (II) with 1-R-hydrazine (III), where PY, R and Q have the meanings given above for the compound of formula I and halo is chloro or bromo. Preferred embodiments of this process are those which produce the above-said preferred composition embodiments of formula I preferably using 2-chloro-5-PY-6-Q-nicotinonitrile.

A composition aspect of the invention resides in a cardiotonic composition for increasing cardiac contractility, said composition comprising a pharmaceutically-acceptable carrier and, as the active component thereof, an effective amount of a cardiotonic 1-R-5-PY-6-Q-1H-pyrazolo[3,4-b]pyridin-3-amine of formula I, where R, PY and Q are each defined as in formula I, or pharmaceutically-acceptable acid-addition salt thereof. Preferred embodiments are those having as active components the above-said preferred embodiments of formula I.

A method aspect of the invention resides in the method for increasing cardiac contractility in a patient requiring such treatment which comprises administering orally or parenterally in a solid or liquid dosage form to such patient an effective amount of a cardiotonic 1-R-5-PY-6-Q-1H-pyrazolo[3,4-b]pyridin-3-amine of formula I where PY, R and Q are defined as in formula I, or pharmaceutically-acceptable acid-addition salt thereof. Preferred embodiments of this method aspect are those using the preferred cardiotonics of formula I noted above.

The term "lower-alkyl" as used herein, e.g., as one of the meanings for R or Q or as a substituent for PY in formula I, means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY in formula I where PY is 4-, 3- or 2-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl" as used herein, e.g., for one of the meanings for R in formula I, means hydroxy-alkyl radicals having from two to six carbon atoms which can be arranged as straight or branched chains and at least two carbon atoms of which separate hydroxy and the 1-ring nitrogen atom of the pyrazolo[3,4-b]pyridine ring, illustrated by 2-hydroxyethyl, 3-hydroxypropyl, 2-hydroxypropyl, 4-hydroxybutyl, 3-hydroxybutyl, 5-hydroxyamyl, 6-hydroxyhexyl, and the like.

The term "lower-alkoxyalkyl" as used herein, e.g., for one of the meanings for R in formula I, means alkoxyalkyl radicals having from three to six carbon atoms which can be arranged as straight or branched chains and at least two carbon atoms of which separate the oxygen atom of alkoxyalkyl and the 1-ring nitrogen atom of the pyrazolo[3,4-b]pyridine ring, illustrated by 2-methoxyethyl, 2-ethoxyethyl, 3-methoxypropyl, 2-methoxypropyl, 2-methoxybutyl, 4-ethoxybutyl, 3-ethoxypropyl, 3-n-propoxypropyl, and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form or the hydrochloride salt; however, appropriate pharmaceutically-acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrobromide sulfate, phosphate, sulfamate, acetate, citrate, lactate, tartrate, methanesulfonate, ethanesulfonate, benzenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I) are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structure of the compound of formula I was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

The preparation of 1-R-5-PY-6-Q-1H-pyrazolo[3,4-b]pyridin-3-amine (I) by reacting 2-halo-5-PY-6-Q-nicotinonitrile (II) with 1-R-hydrazine (III) is carried out by heating the reactants in a suitable solvent at about 50° C. to 100° C., preferably about 65° C. to 85° C., where R, PY and Q have the meanings given above for formula I and halo is chloro or bromo, preferably chloro. The reaction is conveniently run by refluxing the reactants in a lower-alkanol, preferably methanol or ethanol. Other suitable solvents include isopropyl alcohol, dioxane, tetrahydrofuran, dimethylformamide, and the like.

The intermediate 2-halo-5-PY-6-Q-nicotinonitrile (II) is readily prepared by reacting a 1,2-dihydro-2-oxo-5-PY-6-Q-nicotinonitrile with an inorganic halogenating agent preferably by heating the 2-oxo-nicotinonitrile with excess phosphorus oxychloride, conveniently run at reflux temperature (about 107° C.), using a catalytic or small quantity of dimethylformamide. Optionally, a greater quantity of dimethylformamide can be used as solvent; other suitable inert aprotic solvents also can be used, e.g., acetonitrile, dioxane, tetrahydrofuran, and the like. Other suitable inorganic halogenating agents include $PCl_3$, $PCl_5$, $PBr_3$, and the like.

The preparation of known 1,2-dihydro-2-oxo-5-PY-nicotinonitriles is shown in Lesher and Opalka U.S. Pat. No. 4,004,012, issued Jan. 18, 1977.

The preparation of 1,2-dihydro-2-oxo-5-PY-6-(lower-alkyl)nicotinonitriles, which are disclosed and claimed in copending U.S. Patent Application Ser. No. 97,504, filed Nov. 26, 1979, is described generally in the following three paragraphs and is illustrated further hereinbelow in Examples C-1 through C-11 and D-1 through D-11.

The preparation of 1-PY-2-(dimethylamino)ethenyl lower-alkyl ketone by reacting PY-methyl lower-alkyl ketone with dimethylformamide di-(lower-alkyl) acetal is carried out by mixing the reactants in the presence or absence of a suitable solvent. The reaction is conveniently run at room temperature, i.e., about 20°-25° C., or by warming the reactants up to about 100° C., preferably in an aprotic solvent, conveniently hexamethylphosphoramide because of the method used to prepare the PY-methyl lower-alkyl ketone, as noted below in Example C-1. Other suitable solvents include tetrahydrofuran, dimethylformamide, acetonitrile, ether, benzene, dioxane, and the like. Also, the reaction can be run using no solvent, preferably using an excess of dimethylformamide di-(lower-alkyl)acetal.

The intermediate PY-methyl lower-alkyl ketones are generally known compounds which are prepared by known methods [e.g., as given in Rec. trav. chim 72, 522 (1953); U.S. Pat. No. 3,133,077 (5-12-64); Bull. Soc. Chim. France 1968, 4132; Chem. Abstrs. 79, 8539h (1973); Chem. Abstrs. 81, 120,401a (1974); J. Org. Chem. 39, 3834 (1974); Chem. Abstrs. 87, 6594q (1977); J. Org. Chem. 43, 2286 (1978)].

The reaction of 1-PY-2-(dimethylamino)ethenyl lower-alkyl ketone with α-cyanoacetamide to produce 1,2-dihydro-2-oxo-5-PY-6-Q-nicotinonitrile is carried out preferably by heating the reactants in a suitable solvent in the presence of a basic condensing agent. The reaction is conveniently run using an alkali lower-alkoxide, preferably sodium methoxide or ethoxide, in dimethylformamide. In practicing the invention, the reaction is carried out in refluxing dimethylformamide using sodium methoxide. Alternatively, methanol and sodium methoxide or ethanol and sodium ethoxide can be used as solvent and basic condensing agent, respectively; however, a longer heating period is required. Other basic condensing agents and solvents include sodium hydride, lithium diethylamide, lithium diisopropylamide, and the like, in an aprotic solvent, e.g., tetrahydrofuran, acetonitrile, ether, benzene, dioxane, and the like.

The following examples will further illustrate the invention without, however, limiting it thereto.

A. 2-HALO-5-PY-6-Q-NICOTINONITRILES

A-1. 2-Chloro-5-(4-pyridinyl)nicotinonitrile

A mixture containing 127 g. of 1,2-dihydro-2-oxo-5-(4-pyridinyl)nicotinonitrile, 800 ml. of phosphorous oxychloride and 12 ml. of dimethylformamide was refluxed for 4 hours, cooled and the excess phosphorous oxychloride and dimethylformamide was distilled off in vacuo. The remaining residue was poured into ice and the aqueous mixture was basified with ammonium hydroxide solution with cooling. The separated product was collected, washed with water, dried, recrystallized from dimethylformamide, washed successively with methanol and ether and vacuum-dried at 60° C. to yield 114 g. of 2-chloro-5-(4-pyridinyl)nicotinonitrile. A 20 g. portion of this product was recrystallized the second time from dimethylformamide, washed successively with methanol and ether and vacuum-dried at 60° C. to yield 16 g. of 2-chloro-5-(4-pyridinyl)nicotinonitrile, m.p. 224°–227° C. with decomposition.

Following the procedure described in Example A-1 but using in place of 1,2-dihydro-2-oxo-5-(4-pyridinyl)-nicotinonitrile a molar equivalent quantity of the appropriate 1,2-dihydro-2-oxo-5-PY-nicotinotrile, it is contemplated that the corresponding 2-chloro-5-PY-nicotinonitriles of Examples A-2 through A-7 can be obtained.

A-2. 2-Chloro-5-(3-pyridinyl)nicotinonitrile.
A-3. 2-Chloro-5-(2-methyl-3-pyridinyl)nicotinonitrile.
A-4. 2-Chloro-5-(5-methyl-3-pyridinyl)nicotinonitrile.
A-5. 2-Chloro-5-(3-ethyl-4-pyridinyl)nicotinonitrile.
A-6. 2-Chloro-5-(2-methyl-4-pyridinyl)nicotinonitrile.
A-7. 2-Chloro-5-(2,6-dimethyl-4-pyridinyl)-nicotinonitrile.

Following the procedure described in Example A-1 but using in place of phosphorus oxychloride a molar equivalent quantity of the appropriate halogenating agent, it is contemplated that the designated 2-halo-5-(4-pyridinyl)nicotinonitrile of Examples A-8 or A-9 can be obtained.

A-8. 2-Bromo-5-(4-pyridinyl)nicotinonitrile using phosphorus tribromide or phosphorus oxybromide.
A-9. 2-Chloro-5-(4-pyridinyl)nicotinonitrile using phosphorus trichloride, phosphorus pentachloride or sulfuryl chloride.

Following the procedure described in Example A-1 but using in place of 1,2-dihydro-2-oxo-5-(4-pyridinyl)-nicotinonitrile a molar equivalent quantity of the appropriate 1,2-dihydro-2-oxo-5-PY-6-Q-nicotinonitrile, it is contemplated that the corresponding 2-chloro-5-PY-6-Q-nicotinonitriles of Examples A-10 through A-20 can be obtained.

A-10. 2-Chloro-6-methyl-5-(4-pyridinyl)nicotinonitrile.
A-11. 2-Chloro-6-ethyl-5-(4-pyridinyl)nicotinonitrile.
A-12. 2-Chloro-6-methyl-5-(3-pyridinyl)nicotinonitrile.
A-13. 2-Chloro-6-n-propyl-5-(4-pyridinyl)nicotinonitrile.
A-14. 2-Chloro-6-isopropyl-5-(4-pyridinyl)-nicotinonitrile.
A-15. 6-n-Butyl-2-chloro-5-(4-pyridinyl)nicotinonitrile.

A-16. 2-Chloro-6-isobutyl-5-(4-pyridinyl)nicotinonitrile.

A-17. 2-Chloro-5-(4-pyridinyl)-6-tert.-butylnicotinonitrile.

A-18. 2-Chloro-6-n-pentyl-5-(4-pyridinyl)nicotinonitrile.

A-19. 6-Ethyl-2-chloro-5-(2-methyl-4-pyridinyl)nicotinonitrile.

A-20. 6-Ethyl-2-chloro-5-(3-pyridinyl)nicotinonitrile.

B.
5-(PY)-6-Q-1H-PYRAZOLO[3,4-b]PYRIDIN-3-AMINES

B-1. 5-(4-pyridinyl)-1H-pyrazolo[3,4-b]pyridin-3-amine

To a suspension containing 104 g. of 2-chloro-5-(4-pyridinyl)nicotinonitrile in 2 liters of ethanol was added in a rapid stream 100 ml. of 100% hydrazine hydrate. The resulting mixture was refluxed with stirring for 2 hours and then cooled to room temperature. The separated solid was collected, sucked fairly dry on the funnel, dissolved in 750 ml. of hot dimethylformamide and placed in a refrigerator over the weekened. Since the material had crystallized as a very hard mass on the walls of the flask, the mixture was warmed to redissolve the solid. The solution was concentrated in vacuo and the concentrated solution cooled in an ice bath with stirring. The separated solid was collected and the filtrate was concentrated in vacuo to obtain a second crop. The combined crops were slurried with water, collected, dried in vacuo and recrystallized again from dimethylformamide, dried in a vacuum oven at 60° C. for 5 hours to produce 33 g. of 5-(4-pyridinyl)-1H-pyrazolo[3,4-b]pyridin-3-amine, m.p. 291°–293° C.

Following the procedure of Example B-1 but using a molar equivalent quantity of 2-bromo-5-(4-pyridinyl)-nicotinonitrile in place of 2-chloro-5-(4-pyridinyl)-nicotinonitrile, it is contemplated that 5-(4-pyridinyl)-1H-pyrazolo[3,4-b]pyridin-3-amine can be obtained.

The diacetyl derivative of Example B-1 was prepared as a characterizing derivative as follows: A suspension containing 5.3 g. of 5-(4-pyridinyl)-1H-pyrazolo[3,4-b]pyridin-3-amine, 25 ml. of acetic anhydride and a few mg. of p-toluenesulfonic acid was heated with stirring on a steam bath for 2 hours and then allowed to stand overnight at room temperature. About 50 ml. of ether was added to the mixture which was shaken well. The solid was collected, washed with a small amount of fresh ether and air-dried to yield 7.3 g. of solid. The solid was titrated with water and ammonium hydroxide was added until the mixture remained basic. The solid was collected, washed with water and sucked dry. The solid was then recrystallized from 90 ml. of dimethylformamide using decolorizing charcoal and was then washed with ether and dried in a vacuum oven to yield 2.3 g. of N-[1-acetyl-5-(4-pyridinyl)-1H-pyrazolo[3,4b-]pyridin-3-yl]acetamide, m.p. >305° C.

B-2.
1-Methyl-5-(4-pyridinyl)-1H-pyrazolo[3,4-b]pyridin-3-amine

A mixture containing 21.6 g. of 2-chloro-5-(4-pyridinyl)nicotinonitrile, 22 ml. of 1-methylhydrazine and 300 ml. of methanol was refluxed with stirring on a steam bath for 24 hours and then allowed to stand at room temperature overnight. The mixture was cooled well in an ice bath and the golden-yellow solid was collected, washed with ethanol and air-dried to produce 20.8 g. of 1-methyl-5-(4-pyridinyl)-1H-pyrazolo[3,4-b]pyridin-3-amine, m.p. 260°–261° C.

Following the procedure described in Example B-2 but using in place of 1-methylhydrazine a molar equivalent quantity the appropriate 1-R-hydrazine, it is contemplated that the corresponding 1-R-5-(4-pyridinyl)-1H-pyrazolo[3,4-b]pyridin-3-amines of Examples B-3 through B-13 can be obtained.

B-3. 1-Ethyl-5-(4-pyridinyl)-1H-pyrazolo[3,4-b]pyridin-3-amine using 1-ethylhydrazine.

B-4. 1-n-Propyl-5-(4-pyridinyl)-1H-pyrazolo[3,4-b]pyridin-3-amine using 1-n-propylhydrazine.

B-5. 1-Isopropyl-5-(4-pyridinyl)-1H-pyrazolo[3,4-b]pyridin-3-amine using 1-isoproplhydrazine.

B-6. 1-n-butyl-5-(4-pyridinyl)-1H-pyrazolo[3,4-b]pyridin-3-amine using 1-n-butylhydrazine.

B-7. 1-Isobutyl-5-(4-pyridinyl)-1H-pyrazolo[3,4-b]pyridin-3-amine using 1-isobutylhydrazine.

B-8. 1-(2-Butyl)-5-(4-pyridinyl)-1H-pyrazolo[3,4-b]pyridin-3-amine using 1-(2-butyl)hydrazine.

B-9. 1-(n-Amyl)-5-(4-pyridinyl)-1H-pyrazolo[3,4-b]pyridin-3-amine using 1-(n-amyl)hydrazine.

B-10. 1-(n-Hexyl)-5-(4-pyridinyl)-1H-pyrazolo[3,4-b]pyridin-3-amine using 1-(n-hexyl)hydrazine.

B-11. 1-(2-Ethoxyethyl)-5-(4-pyridinyl)-1H-pyrazolo[3,4-b]pyridin-3-amine using 1-(2-ethoxyethyl)-hydrazine.

B-12. 1-(2-Methoxyethyl)-5-(4-pyridinyl)-1H-pyrazolo[3,4-b]pyridin-3-amine using 1-(2-methoxyethyl)hydrazine.

B-13. 1-(3-Methoxypropyl)-5-(4-pyridinyl)-1H-pyrazolo[3,4-]pyridin-3-amine using 1-(3-methoxypropyl)hydrazine.

Following the procedure in Example B-1 or B-2 but using in place of 2-chloro-5-(4-pyridinyl)-nicotinonitrile and hydrazine or 1-methylhydrazine, respectively, corresponding molar equivalent quantities of the respective appropriate 2-chloro-5-PY-nicotinonitrile and 1-R-hydrazine, it is contemplated that there can be obtained the corresponding 1-R-5-PY-1H-pyrazolo[3,4-b]pyridin-3-amines of Examples B-14 through B-19.

B-14. 1-Methyl-5-(3-pyridinyl)-1H-pyrazolo[3,4-b]pyridin-3-amine.

B-15. 5-(2-Methyl-3-pyridinyl)-1H-pyrazolo[3,4-b]pyridin-3-amine.

B-16. 1-Ethyl-5-(5-methyl-3-pyridinyl)-1H-pyrazolo-[3,4-b]pyridin-3-amine.

B-17. 1-Methyl-5-(3-ethyl-4-pyridinyl)-1H-pyrazolo[3,4-b]pyridin-3-amine.

B-18. 1-(2-Methoxyethyl)-5-(2-methyl-4-pyridinyl)-1H-pyrazolo[3,4-b]pyridin-3-amine.

B-19. 1-Methyl-5-(2,6-dimethyl-4-pyridinyl)-1H-pyrazolo[3,4-b]pyridin-3-amine.

B-20.
3-Amino-5-(4-pyridinyl)-1H-pyrazolo[3,4-b]pyridine-1-ethanol

To a suspension containing 33.9 g. of 2-chloro-5-(4-pyridinyl)nicotinonitrile and 650 ml. of methanol was added 55 ml. of 1-(2-hydroxyethyl)hydrazine and the resulting mixture was refluxed with stirring for 24 hours and the mixture then allowed to stand at room temperature overnight. The mixture was cooled well in an ice bath and the cottony-yellow solid was collected, recrystallized from 1600 ml. of absolute ethanol and the resulting bright yellow solid was dried in a vacuum oven for 5 hours at 90° C. to yield 28.2 g. of 3-amino-5-(4- pyridinyl)-1H-pyrazolo[3,4-b]pyridine-1ethanol, m.p. 217°-217.5° C.

Following the procedure described in Example B-20 but using in place of 2-chloro-5-(4-pyridinyl)nicotinonitrile and 1-(2-hydroxyethyl)hydrazine corresponding molar equivalent quantitites of the appropriate 2-chloro-5-PY-nicotinonitrile and 1-(lower-hydroxyalkyl)-hydrazine, it is contemplated that the 3-amino-5-PY-1H-pyrazolo[3,4-b]pyridine-1-(lower-alkanols) of Example B-20 through B-26 can be obtained.

B-21.  3-Amino-5-(3-pyridinyl)-1H-pyrazolo[3,4-b]pyridine-1-ethanol.

B-22.  3-Amino-5-(2-methyl-3-pyridinyl)-1H-pyrazolo[3,4-b]pyridine-1-ethanol.

B-23.  3-Amino-5-(5-methyl-3-pyridinyl)-1H-pyrazolo[3,4-b]pyridine-1-(n-propanol).

B-24.  3-Amino-5-(4-pyridinyl)-1H-pyrazolo[3,4-b]pyridine-1-(2-propanol).

B-25.  3-Amino-5-(3-ethyl-4-pyridinyl)-1H-pyrazolo[3,4-b]pyridine-1-(2-butanol).

B-26.  3-Amino-5-(2-methyl-4-pyridinyl)-1H-pyrazolo[3,4-b]pyridine-1-ethanol.

B-27.  3-Amino-5-(2,6-dimethyl-4-pyridinyl)-1H-pyrazolo[3,4-b]pyridine-1-ethanol.

Following the procedure described in Example B-20 but using in place of 2-chloro-5-(4-pyridinyl)nicotinonitrile and/or 1-(2-hydroxyethyl)hydrazine molar equivalent quantities of the appropriate 2-chloro-5-PY-6-(lower-alkyl)nicotinonitrile and/or 1-R-hydrazine, respectively, it is contemplated that the corresponding 1-R-5-PY-6-Q-1H-pyrazolo[3,4-b]pyridin-3-amines of Examples B-28 through B-41 can be obtained.

B-28. 1,6-Dimethyl-5-(4-pyridinyl)-1H-pyrazolo[3,4-b]pyridin-3-amine.

B-29.  6-Ethyl-1-methyl-5-(4-pyridinyl)-1H-pyrazolo[3,4-b]pyridin-3-amine.

B-30.  6-Methyl-5-(4-pyridinyl)-1H-pyrazolo[3,4-b]pyridin-3-amine.

B-31.  1-Ethyl-6-methyl-5-(3-pyridinyl)-1H-pyrazolo[3,4-b]pyridin-3-amine.

B-32.  3-Amino-6-methyl-5-(4-pyridinyl)-1H-pyrazolo[3,4-b]pyridine-1-ethanol.

B-33.  3-Amino-6-ethyl-5-(4-pyridinyl)-1H-pyrazolo[3,4-b]pyridine-1-ethanol.

B-34.  1-Methyl-6-n-propyl-5-(4-pyridinyl)-1H-pyrazolo[3,4-b]pyridin-3-amine.

B-35.  6-Isopropyl-5-(4-pyridinyl)-1H-pyrazolo[3,4-b]pyridin-3-amine.

B-36.  6-n-Butyl-1-methyl-5-(4-pyridinyl)-1H-pyrazolo[3,4-b]pyridin-3-amine.

B-37.  3-Amino-6-isobutyl-5-(4-pyridinyl)-1H-pyrazolo[3,4-b]pyridine-1-ethanol.

B-38.  5-(4-Pyridinyl)-6-tert.-butyl-1H-pyrazolo[3,4-b]pyridin-3-amine.

B-39.  1-Methyl-6-n-pentyl-5-(4-pyridinyl)-1H-pyrazolo[3,4-b]pyridin-3-amine.

B-40.  1,6-Diethyl-5-(2-methyl-4-pyridinyl)-1H-pyrazolo[3,4-b]pyridin-3-amine.

B-41.  3-Amino-6-ethyl-5-(3-pyridinyl)-1H-pyrazolo[3,4-b]pyridine-1-ethanol.

Following the procedure described in Example B-20 but using in place of 1-(2-hydroxyethyl)hydrazine a corresponding molar equivalent quantity of 1-(2,3-dihydroxypropyl)hydrazine and either 2-chloro-5-(4-pyridinyl)nicotinonitrile or a corresponding molar equivalent quantity of the appropriate 2-chloro-5-PY-6-Q-nicotinonitrile, it is contemplated that there can be obtained the 1-(2,3-dihydroxypropyl)-5-PY-6-Q-1H-pyrazolo[3,4-b]pyridin-2-amines of Examples B-42 through B-44.

B-42.  1-(2,3-Dihydroxypropyl)-5-(4-pyridinyl)-1H-pyrazolo[3,4-b]pyridin-3-amine.

B-43.  1-(2,3-Dihydroxypropyl)-6-methyl-5-(4-pyridinyl)-1H-pyrazolo[3,4-b]pyridin-3-amine.

B-44.  1-(2,3-Dihydroxypropyl)-5-(3-pyridinyl)-1H-pyrazolo[3,4-b]pyridin-3-amine.

C. 1-PY-2-(DIMETHYLAMINO)ETHENYL LOWER-ALKYL KETONES

C-1. 1-(4-Pyridinyl)-2-(dimethylamino)ethenyl methyl ketone

A mixture containing 20 g. of (4-pyridinyl)methyl methyl ketone [alternatively named 1-(4-pyridinyl)-2-propanone] and 30 cc. of hexamethylphosphoramide was diluted with 65 cc. of dimethylformamide dimethyl acetal and the resulting mixture was refluxed for 30 minutes. TLC analysis showed a single spot, thereby indicating completion of the reaction (in another run, the reaction appeared to be complete after 30 minutes at room temperature). The reaction mixture was evaporated under reduced pressure using a rotary vaporizer and a pressure of about 0.5 mm., thereby resulting in a crystalline residue weighing 24 g. The residue was decolorized during continuous column chromatography on alumina (about 150 g. of alumina in a 500 cc. a continuous separating funnel) using refluxing chloroform. After 1 and ½ hours, the extract was heated in vacuo to remove the chloroform, thereby leaving, as a light yellow crystalline material, 23.2 g. of 1-(4-pyridinyl)-2-(dimethylamino)ethenyl methyl ketone, alternatively named 3-dimethylamino-4-(4-pyridinyl)-3-buten-2-one.

The above preparation can be carried out using in place of hexamethylphosporamide other solvents, e.g., dimethyformamide, acetonitrile or others noted above; however, hexamethylphosphoramide was conveniently used since (4-pyridinyl)methyl methyl ketone was conventionaly prepared as a mixture together with hexamethylphosphoramide, as seen by the following preparation: To a stirred solution containing 70 cc. of freshly distilled diisopropylamine and 200 cc. of tetrahydrofuran at 0° C. under nitrogen was added dropwise over 20 minutes 210 cc. of 2.4 M n-butyllithium in n-hexane and the reaction mixture was stirred for about 35 minutes at about 0°-5° C. To the cold solution was added dropwise over a period of 10 minutes 90 cc. of dry hexamethylphosphoramide (no temperature change) and a resulting light yellow solution was stirred for 15 minutes. To the cold solution at 0° C. was added a solution of 50 cc. of 4-picoline in 150 cc. of dry tetrahydrofuran over a 15 minute period and stirring was continued for 30 minutes at 0° C. Next, a mixture containing 50 cc. of dry ethyl acetate and 150 cc. of tetrahydrofuran was added over a 15 minute period (temperature rose from 0° to about 6° C.) and the resulting mixture was stirred for 20 minutes at 0° C. The ice bath was then removed and stirring continued for another 90 minutes whereupon the temperature of the reaction mixture rose to about 25° C. The reaction mixture was then cooled in an ice bath and to it was added 60 cc. of acetic acid over a period of about 30 minutes. The tetrahydrofuran was distilled off using a rotary vaporizer in vacuo. The remaining mixture was diluted with 400 cc. of water and the aqueous mixture was extracted successively with two 250 cc. portions of isopropyl acetate and three 80 cc. portions of chloroform. The solvents were distilled off under reduced pressure to yield about 137 g. of mixture consisting primarily of the desired product and hexamethylphosphormaide. Another run using the same quantities was carried out as above except after the addition of 60 cc. of glacial acetic acid, the mixture was diluted with only 200 cc. of water, the phases were separated, and the aqueous phase was extracted with five 100 ml. portions of chloroform. The chloroform extract was washed with saline solution and the chloroform was distilled off in vacuo. The remaining mixture of the desired ketone and hexamethylphosphoramide was combined with the above 137 g. of the same mixture and the combined mixture was distilled under reduced pressure to yield the following fractions: I. 63 g., b.p. of 110°–112° C. at 4 mm.; II. 59 g. of pale yellow oil, b.p. 113°–115° C. at 3 mm.; and, III. 69 g. of pale yellow oil, b.p. 115°–118° C. at 2.5 mm. Examination of fraction III by NMR showed it to contain 2:3 mixture by weight of (4-pyridinyl)methyl methyl ketone and hexamethylphosphoramide.

Acid-addition salts of 1-(4-pyridinyl)-2-(dimethylamino)ethenyl methyl ketone are conveniently prepared by adding to a mixture of 5 g. of 1-(4-pyridinyl)-2-(dimethylamino)ethenyl methyl ketone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1-(4-pyridinyl)-2-(dimethylamino)ethenyl methyl ketone and the appropriate acid, e.g., lactic acid or hydrochloric acid, to prepare respectively the monolactate or monohydrochloride salt in aqueous solution.

C-2. 1-(4-Pyridinyl)-2-(dimethylamino)ethenyl ethyl ketone

A mixture containing 87.5 g. of (4-pyridinyl)methyl ethyl ketone [alternatively named 1-(4-pyridinyl)-2-butanone] and 160 cc. of hexamethylphosphoramide was diluted with 100 g. of dimethylformamide dimethyl acetal and the resulting mixture was stirred under nitrogen at room temperature for 45 minutes. The methanol formed by the reaction was distilled off in vacuo using a rotary evaporator and the remaining material was distilled under reduced pressure to yield two fractions, one boiling at 45°–80° C. at 0.5 mm. and the second at 90°–95° C. at 0.5 mm. After TLC analysis showed predominanly only a single spot for each fraction, the two fractions were combined (135 g.) and taken up in 600 cc. of chloroform. The resulting solution was washed with two 300 cc. portions of water and the water was back extracted with three 100 cc. portions of chloroform. The combined chloroform solution was dried over anhydrous sodium sulfate and decolorized by running it through 300 cc. of alumina in a 500 cc. continuous extraction funnel followed by extraction with refluxing chloroform. The chloroform was distilled off in vacuo to yield a red oil which crystallized on standing overnight in an ice bath. The crystalline material was dissolved in carbon tetrachloride, cylohexane was added and the mixture cooled to yield 64 g. of the resulting yellow crystalline product, 1-(4-pyridinyl)-2-(dimethylamino)ethenyl ethyl ketone. Another 11 g. of crystalline product was obtained by passing the mother liquor through the continuous extraction column and using refluxing chloroform as the solvent.

The above intermediate (4-pyridinyl)methyl ethyl ketone was obtained in a mixture with hexamethylphosphoramide as follows: To a mixture containing 200 cc. of tetrahydrofuran and 70 cc. of diisopropylamine under nitrogen at 0°–5° C. was added 210 c. of 2.4 N n-butyllithium in n-hexane and the resulting mixture was stirred for 30 minutes. Next was added over a 10 minute period 90 cc. of hexamethylphosphoramide followed by stirring of the mixture for 15 minutes. Then was added over a 15 minute period a solution of 48 cc. of 4-picoline in 150 cc. of tetrahydrofuran followed by stirring for 30 minutes at about 0° C. The ice/acetone bath cooling the reaction mixture was replaced with a dry ice/acetone bath and to the reaction mixture was added over a 20 minute period a mixture of 75 cc. of ethyl propionate in an equal volume of tetrahydrofuran. The reaction mixture was then allowed to warm up to room temperature over a period of about 90 minutes and then was warmed at about 35° C. for 30 minutes. The mixture was next cooled in an ice/acetone bath and to it was added 60 cc. of glacial acetic acid over 30 minutes. The resulting pale yellow suspension was diluted with 200 cc. of water. The mixture was extracted with three 150 cc. portions of ethyl acetate and the ethyl acetate extract was back washed with saline solution. The extract was heated in vacuo to remove the ethyl acetate and the residue was taken up again with ethyl acetate. The solution was washed with water and then heated in vacuo to remove the ethyl acetate followed by heating the residue in vacuo at 50° C. for about 30 minutes to yield 100 g. of pale yellow oil. The pale yellow oil was combined with corresponding samples obtained from two additional runs and then distilled in vacuo to yield a 256 g. fraction, b.p. 85°–105° C. at 0.5–1.0mm. The NMR of this fraction showed it to be a mixture of (4-pyridinyl)methyl ethyl ketone and hexamethylphosphoramide in a respective molar ratio of 1:1.55, that is, 35% or 0.35×256=90 g. of said ketone.

Following the procedure described in Example C-2 but using a molar equivalent quantity of the appropriate PY-methyl lower-alkyl ketone (II) in place of (4-pyridinyl)methyl ethyl ketone, it is contemplated that the corresponding 1-PY-2-(dimethylamino)ethenyl lower-alkyl ketones of Examples C-3 thru C-17 can be obtained.

C-3. 1-(3-Pyridinyl)-2-(dimethylamino)ethenyl methyl ketone using (3-pyridinyl)methyl methyl ketone.

C-4. 1-(4-Pyridinyl)-2-(dimethylamino)ethenyl n-propyl ketone using (4-pyridinyl)methyl n-propyl ketone.

C-5. 1-(4-Pyridinyl)-2-(dimethylamino)ethenyl isopropyl ketone using (4-pyridinyl)methyl isopropyl ketone.

C-6. 1-(4-Pyridinyl)-2-(dimethylamino)ethenyl n-butyl ketone using (4-pyridinyl)methyl n-butyl ketone.

C-7. 1-(4-Pyridinyl)-2-(dimethylamino)ethenyl isobutyl ketone using (4-pyridinyl)methyl isobutyl ketone.

C-8. 1-(4-Pyridinyl)-2-(dimethylamino)ethenyl tert.-butyl ketone using (4-pyridinyl)methyl tert.-butyl ketone.

C-9. 1-(4-Pyridinyl)-2-(dimethylamino)ethenyl n-pentyl ketone using (4-pyridinyl)methyl n-pentyl ketone.

C-10. 1-(2-Methyl-4-pyridinyl)-2-(dimethylamino)ethenyl ethyl ketone using (2-methyl-4-pyridinyl)methyl ethyl ketone.

C-11. 1-(3-Pyridinyl)-2-(dimethylamino)ethenyl ethyl ketone using (3-pyridinyl)methyl ethyl ketone.

D. 1,2-DIHYDRO-6-(LOWER-ALKYL)-2-OXO-5-PY-NICOTINONITRILES

D-1.
1,2-Dihydro-6-methyl-2-oxo-5-(4-pyridinyl)nicotinonitrile

Alternatively named 1,6-dihydro-2-methyl-6-oxo-[3,4'-bipyridine]-5-carbonitrile—To a mixture containing 23 g. of 1-(4-pyridinyl)-2-(dimethylamino)ethenyl methyl ketone and 11 g. of α-cyanoacetamide dissolved in 400 cc. of dimethylformamide was added with stirring 14 g. of sodium methoxide and the resulting reaction mixture was heated in an oil bath under gentle reflux for one hour. TLC analysis showed no starting material in the reaction mixture which was then concentrated in vacuo on a rotary vaporator to a volume of about 80 cc. The concentrate was treated with about 160 cc. of acetonitrile and the resulting mixture was stirred on a rotary vaporator with warming until homogenuous and then cooled. The crystalline product was collected, rinsed successively with acetonitrile and ether, and dried overnight at 55° C. to yield 28 g. of tan crystalline product, namely, sodium salt of 1,2-dihydro-6-methyl-2-oxo-5-(4-pyridinyl)nicotinonitrile, the presence of cyano being confirmed by IR analysis. An 8 g. portion of said sodium salt was dissolved in 75 cc. of hot water, the aqueous solution treated with decolorizing charcoal filtered, the filtrate again treated with decolorizing charcoal and filtered, and the filtrate acidified with 6 N hydrochloric acid by dropwise addition to a pH of 3. The acidic mixture was diluted with ethanol and cooled. The crystalline product was collected, dried, recrystallized from dimethylformamide-water and dried to produce 3.75 g. of 1,2-dihydro-6-methyl-2-oxo-5-(4-pyridinyl)nicotinonitrile, m.p. 300° C.

Acid-addition salts of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile in about 40 ml. of aqueous methanol the appropriate acid, e.g., methanesulfonic acid, concentrated sulfuric acid, concentrated phosphoric acid, to a small pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)nicotinonitrile and the appropriate acid, e.g., lactic acid or hydrochloric acid, to prepare respectively the monolactate or monohydrochloride salt in aqueous solution.

D-2.
6-Ethyl-1,2-dihydro-2-oxo-5-(4-pyridinyl)nicotinonitrile

Alternatively named 2-ethyl-1,6-dihydro-6-oxo-[3,4'-bipyridine]-5-carbonitrile, m.p. >300° C., 11.6 g., was prepared following the procedure described above in Example D-1 using 20 g. of 1-(4-pyridinyl)-2-(dimethylamino)ethenyl ethyl ketone, 8.4 g. of α-cyanoacetamide, 16.2 g. of sodium methoxide and 250 cc. of dimethylacetamide (as solvent in place of dimethylformamide).

Following the procedure described in Example D-2 but using a molar equivalent quantity of the appropriate 1-PY-2-(dimethylamino)ethenyl lower-alkyl ketone in place of 1-(4-pyridinyl)-2-(dimethylamino)ethenyl ethyl ketone, it is contemplated that the corresponding 1,2-dihydro-2-oxo-5-PY-6-R-nicotinonitriles of Examples D-3 thru D-11 can be obtained.

D-3.
1,2-Dihydro-6-methyl-2-oxo-5-(3-pyridinyl)nicotinonitrile

Using 1-(3-pyridinyl)-2-(dimethylamino)ethenyl methyl ketone.

D-4.
1,2-Dihydro-2-oxo-6-n-propyl-5-(4-pyridinyl)-nicotinonitrile

Using 1-(4-pyridinyl)-2-(dimethylamino)ethenyl n-propyl ketone.

D-5.
1,2-Dihydro-6-isopropyl-2-oxo-5-(4-pyridinyl)-nicotinonitrile

Using 1-(4-pyridinyl)-2-(dimethylamino)ethenyl isopropyl ketone.

D-6.
6-n-Butyl-1,2-dihydro-2-oxo-5-(4-pyridinyl)nicotinonitrile

Using 1-(4-pyridinyl)-2-(dimethylamino)ethenyl n-butyl ketone.

D-7.
1,2-Dihydro-6-isobutyl-2-oxo-5-(4-pyridinyl)nicotinonitrile

Using 1-(4-pyridinyl)-2-(dimethylamino)ethenyl isobutyl ketone.

D-8.
1,2-Dihydro-2-oxo-5-(4-pyridinyl)-6-tert.-butyl-nicotinonitrile

Using 1-(4-pyridinyl)-2-(dimethylamino)ethenyl tert.-butyl ketone.

D-9.
1,2-Dihydro-2-oxo-6-n-pentyl-5-(4-pyridinyl)-nicotinonitrile

Using 1-(4-pyridinyl)-2-(dimethylamino)ethenyl n-pentyl ketone.

D-10.
6-Ethyl-1,2-dihydro-5-(2-methyl-4-pyridinyl)-2-oxonicotinonitrile

Using 1-(2-methyl-4-pyridinyl)-2-(dimethylamino)ethenyl ethyl ketone.

D-11.
6-Ethyl-1,2-dihydro-2-oxo-5-(3-pyridinyl)nicotinonitrile

Using 1-(3-pyridinyl)-2-(dimethylamino)ethenyl ethyl ketone.

The usefulness of the compound of formula I, or pharmaceutically-acceptable acid-addition salt thereof, as a cardiotonic agent is demonstrated by its effectiveness in standard pharmacological test procedures, for example, in causing a significant increase in the contractile force of the isolated cat atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the above-noted isolated cat atria and papillary muscle procedure, the compounds of formula I or pharmaceutically-acceptable acid-addition salt thereof at doses of 10, 30, 100 and 300 μg./ml. were found to cause significant increases, that is about 25% or greater, e.g., up to about 150 to 200%, in papillary muscle force and significant increases, that is, about 25% or greater, e.g., up to about 50 to 200%, in right atrial force, while causing only a low percentage increase (about one-half or less than the percentage increase in right atrial force or papillary muscle force) in right atrial rate.

Similarly, when tested by the above-noted anesthetized dog procedure, the compounds of formula I or pharmaceutically-acceptable acid-addition salt thereof at doses of about 1.0, 3.0 and 10.0 mg./kg. administered intravenously were found to cause significant increases, that is, about 25% or greater, in cardiac contractile force or cardiac contractility with lower changes in heart rate and blood pressure.

Preferred embodiments are subjected to further standard cardiotonic test procedures. A particularly preferred embodiment, 3-amino-5-(4-pyridinyl)-1H-pyrazolo[3,4-b]pyridine-1-ethanol, Example B-20, when administered intravenously in a dose range of 0.3 to 3.0 mg./kg. was found to cause dose-dependent increase in cardiac contractile force and lowering in diastolic blood pressure. No significant changes in systolic blood pressure, heart rate or EKG was observed; it had a rapid onset and moderate duration of action. The intravenous infusion of this compound in anesthetized dogs at a rate of 100 μg./kg./min. for three hours resulted in a marked increase in cardiac contractile force within fifty minutes with a peak effect of about sixty to one hundred and twenty minutes. The duration of action of the inotropic response to 3-amino-5-(4-pyridinyl)-1H-pyrazolo[3,4-b]pyridine-1-ethanol after termination of infusion was greater than one hour. The oral administration of 1 to 10 mg./kg. of 3-amino-5-(4-pyridinyl)-1H-pyrazolo[3,4-b]pyridine-1-ethanol in the unanesthetized dog caused dose-dependent increases in cardiotonic contractile force; heart rate increased moderately at a dose of 10 mg./kg., with no significant changes in blood pressure or EKG being observed.

When screened by other standard pharmacological test procedures, 3-amino-5-(4-pyridinyl)-1H-pyrazolo[3,4-b]pyridine-1-ethanol was found to have antihypertensive properties (AHD$_{40}$ of 50 mg./kg. p.o. in the spontaneously hypertensive rat) and bronchodilator activity (100 mg./kg. p.o./inhibition of bronchoconstriction induced by histamine, acetylcholine or immune complex in guinea pigs in vivo). Also, 5-(4-pyridinyl)-1H-pyrazolo[3,4-b]pyridin-3-amine and 1-methyl-5-(4-pyridinyl)-1H-pyrazolo[3,4-b]pyridin-3-amine were found to have comparable bronchodilator activity in the same test procedure.

The present invention includes within its scope a cardiotonic composition for increasing cardiac contractility, said composition comprising a pharmaceutically-acceptable carrier and, as the active component thereof, the cardiotonic 1-R-5-PY-1H-pyrazolo[3,4-b]pyridin-3-amine (formula I) or pharmaceutically-acceptable acid-addition salt thereof. The invention also includes within its scope the method for increasing cardiac contractility in a patient requiring such treatment which comprises administering to such patient an effective amount of said 1-R-5-PY-1H-pyrazolo[3,4-b]pyridin-3-amine (formula I) or pharmaceutically-acceptable acid-addition salt thereof. In clinical practice said compound or salt thereof will normally be administered orally or parenterally in a wide variety of dosage forms.

Solid compositions for oral administration include compressed tablets, pill, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 1-R-5-PY-6-Q-1H-pyrazolo[3,4-b]pyridin-3-amine having the formula

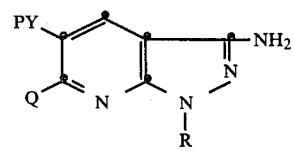

where R is hydrogen, lower-alkyl, lower-hydroxyalkyl having from two to six carbon atoms, 2,3-dihydroxypropyl or lower-alkoxyalkyl having from three to six carbon atoms, Q is hydrogen or lower-alkyl, PY is 4- or 3-pyridinyl or 4- or 3-pyridinyl having one or two lower-alkyl substituents, and where lower-alkyl, all occurrences other than specifically defined above, contains from one to six carbon atoms, or pharmaceutically-acceptable acid-addition salt thereof.

2. A compound according to claim 1 where R is hydrogen.

3. A compound according to claim 1 where R is methyl.

4. A compound according to claim 1 where R is 2-hydroxyethyl.

5. A compound according to claim 1 where PY is 4-pyridinyl or 3-pyridinyl.

6. A compound according to claim 1 where Q is hydrogen or methyl.

7. 3-Amino-5-(4-pyridinyl)-1H-pyrazolo [3,4-b]pyridine-1-ethanol or pharmaceutically-acceptable acid-addition salt thereof.

8. A cardiotonic composition for increasing cardiac contractility, said composition comprising a pharmaceutically-acceptable inert carrier and, as the active component thereof, an effective amount for increasing cardiac contractility of a cardiotonic 1-R-5-PY-6-Q-1H-pyrazolo[3,4-b]pyridine-3-amine or pharmaceutically-acceptable acid-addition salt thereof, where R is hydrogen, lower-alkyl, lower-hydroxyalkyl having from two to six carbon atoms, 2,3-dihydroxypropyl or lower-alkoxyalkyl having from three to six carbon atoms, Q is hydrogen or lower-alkyl, PY is 4 or 3-pyridinyl or 4- or 3-pyridinyl having one or two lower-alkyl substituents, and where lower-alkyl, all occurrences other than specifically defined above, contains from one to six carbon atoms.

9. A composition according to claim 8, where the active component is 3-amino-5-(4-pyridinyl)-1H-pyrazolo[3,4-b]pyridine-1-ethanol or pharmaceutically-acceptable acid-addition salt thereof.

10. The method for increasing cardiac contractility in a patient requiring such treatment which comprises administering orally or parenterally in a solid or liquid dosage form to such patient an effective amount for increasing cardiac contractility of a cardiotonic 1-R-5-PY-6-Q-1H-pyrazolo[3,4-b]pyridin-3-amine or pharmaceutically-acceptable acid-addition salt thereof, where R is hydrogen, lower-alkyl, lower-hydroxyalkyl having from two to six carbon atoms, 2,3-dihydroxypropyl or lower-alkoxyalkyl having from three to six carbon atoms, Q is hydrogen or lower-alkyl, PY is 4- or 3-pyridinyl or 4- or 3-pyridinyl having one or two lower-alkyl substituents, and where lower-alkyl, all occurrences not specifically defined above, contains from one to six carbon atoms.

11. The method according to claim 10 where the cardiotonic is 3-amino-5-(4-pyridinyl)-1H-pyrazolo[3,4-b]pyridine-1-ethanol or pharmaceutically-acceptable acid-addition salt thereof.

* * * * *